United States Patent [19]

Wissman et al.

[11] Patent Number: 4,587,983
[45] Date of Patent: May 13, 1986

[54] METHOD OF INSTALLING AN ARTIFICIAL TOE OR FINGER NAIL AT THE SITE OF THE SURGICAL REMOVAL OF THE NATURAL NAIL

[76] Inventors: Lance R. Wissman, 4554 Poinsettia, S.E., Kentwood, Mich. 49508; Sandra D. Bouwer, 316 Baynton, N.E., Grand Rapids, Mich. 49503; Cheryl L. Jeluso, 2165 Rogue River, Belmont, Mich. 49306

[21] Appl. No.: 591,954

[22] Filed: Mar. 21, 1984

[51] Int. Cl.$^4$ .............................................. A45D 29/00
[52] U.S. Cl. ...................................................... 132/73
[58] Field of Search ....................... 132/73, 73.5, 88.5; 3/1, 12, 12.7; 128/77, 81 R, 81 A, 92 C

[56] References Cited

U.S. PATENT DOCUMENTS

| | | | |
|---|---|---|---|
| 3,981,298 | 9/1976 | Vironda | 128/81 R |
| 4,157,095 | 6/1979 | Sweet | 132/73 |
| 4,222,399 | 9/1980 | Ionescu | 132/73 |
| 4,299,243 | 11/1981 | Umstattd | 132/73 |
| 4,361,160 | 11/1982 | Bryce | 132/73 |
| 4,407,310 | 10/1983 | Jadow | 132/73 |
| 4,445,234 | 5/1984 | Ogunro | 128/81 A |

Primary Examiner—Gene Mancene
Assistant Examiner—Carolyn A. Harrison
Attorney, Agent, or Firm—Glenn B. Morse

[57] ABSTRACT

An initially plastic mass is interposed between an artificial nail and a toe or finger nail bed under gentle pressure, after applying a parting agent to the nail bed. The mass bonds to the nail, and separates from the nail bed at the parting agent as the nail and mass are removed. The parting agent is replaced by a clinical adhesive.

6 Claims, 6 Drawing Figures

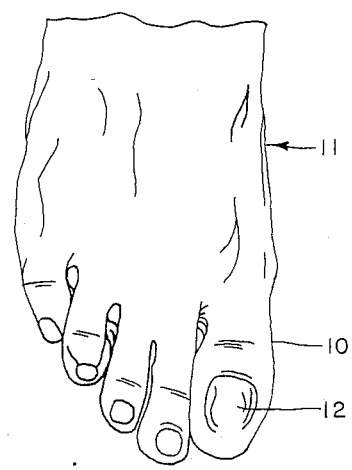
FIG. 1
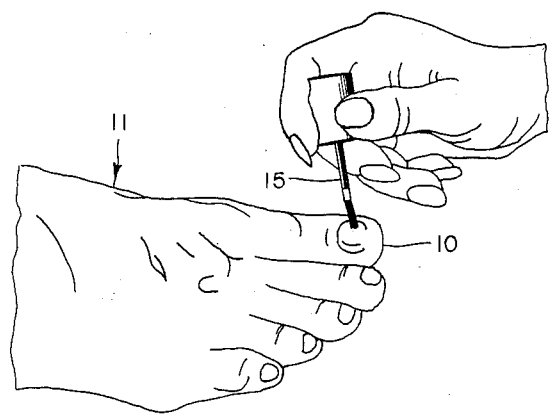
FIG. 2
FIG. 3
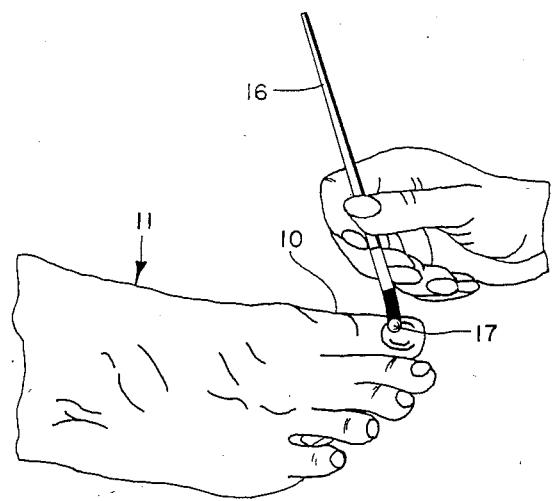

METHOD OF INSTALLING AN ARTIFICIAL TOE OR FINGER NAIL AT THE SITE OF THE SURGICAL REMOVAL OF THE NATURAL NAIL

BACKGROUND OF THE INVENTION

The use of artificial finger nails is commonplace. The nail blanks of thin plastic material are usually adhesively secured to the natural nail for purposes of appearance. Once secured in place, they are trimmed and polished according to preference. The adhesive is usually of a type that can be dissolved with acetone, or some similar solvent, whenever it is desired to replace the artificial nail.

When a finger or toe nail has been surgically removed, the usual procedure for installing an artificial nail cannot be used. The remaining exposed nail bed does not provide a sufficiently uniform surface for the application of an adhesive to bond a nail blank in position. Too much variation in contour exists to be able to provide a sufficiently large set of sizes and shapes to satisfy the individual variations that are commonly encountered. The present invention has been developed to meet this need, which appears to be centered primarily in the installation of artificial nails on the toes.

SUMMARY OF THE INVENTION

The nail bed site of the surgical removal of a toe nail is treated with a parting agent. A curable initially plastic material is applied to the nail bed, and an artificial nail is pressed into position on the nail bed over the plastic material. The plastic material bonds to the nail and remains with it as the nail and plastic material are pulled free from the nail bed at the parting agent. The parting agent is then removed from the nail bed, and from the plastic material, and is replaced by a clinical adhesive. The nail-plastic assembly is then removeably re-positioned on the nail bed.

DESCRIPTION OF THE DRAWINGS

FIG. 1 is a view of the forward portion of a human foot, showing the nail surgically removed from the big toe.

FIG. 2 is a view illustrating the technique of the application of the liquid preparatory materials to the nail bed.

FIG. 3 illustrates the technique of the application of a curable plastic mass to the nail bed.

DESCRIPTION OF THE PREFERRED METHOD

Figure 4:
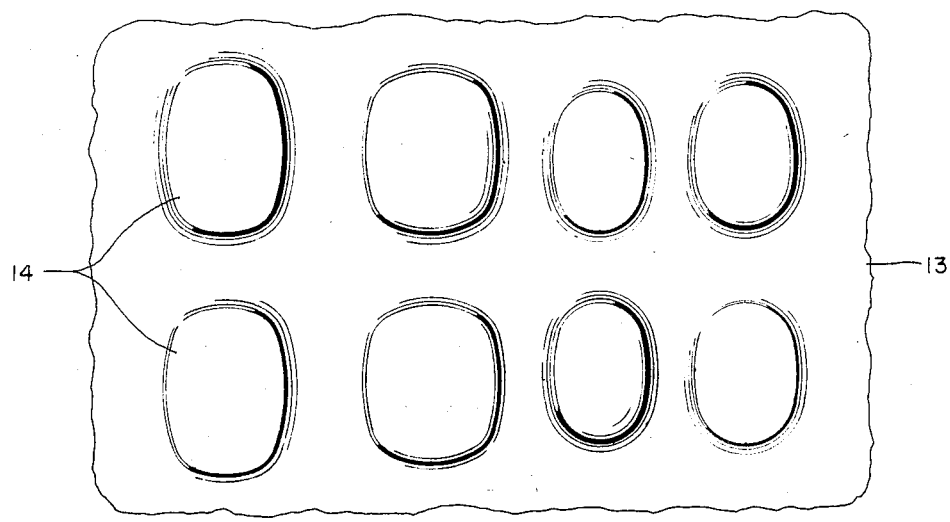
FIG. 4 is a plan view of a plastic sheet containing various configurations of artificial nail blanks.
Figure 5:
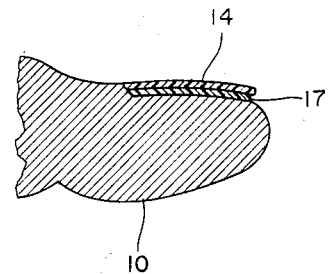
FIG. 5 is a section along the axis of the big toe, showing the artificial nail as installed.
Figure 6:
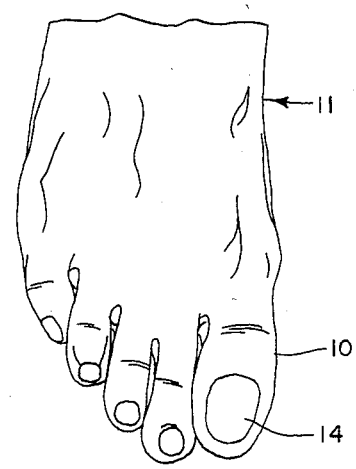
FIG. 6 shows a view of the front portion of the human foot, with the artificial nail fully installed.

The starting point of the method is the condition of the foot illustrated in FIG. 1. The natural nail has been removed from the big toe 10 of the foot 11, leaving the nail bed 12 exposed at the site of the removed nail. A preliminary preparation of the site is preferred, consisting of the application of an astrigent, which is dried with a cotton ball, followed by the application of a drying agent. Antibacterial drops are then applied to prevent development of bacterial growth around the nail bed. These substances can be of any of the standard materials used in clinical procedures. It has also been found effective to combine all three of these in one application by the use of alcohol. This can be applied with a small swab, and blotted as dry as practical, followed by exposure of the nail bed to the air for a few minutes for the natural drying action of the alcohol to be completed. It is most convenient for the operator then to select and cut out an appropriate nail blank from the panel illustrated in FIG. 4. This panel is a sheet of skin tone or translucent acetate, or some similar plastic material, preferably on the order of 0.020 inches in thickness. Various contours are molded in the panel 13, as indicated at 14. A particular one presenting the closest approach to the contour of the nail bed 12 is selected, and cut from the panel 13 with a pair of scissors, possibly accompanied by some degree of trimming. A set of various sizes and shapes of nail blanks can also be made available as separate injection-molded items. After the nail blank has been cut out and trimmed, the back of it should be roughened slightly with an emery board. Any remaining nail growth on the nail bed should also be similarly roughened.

A thin layer of non-adhesive separating medium such as petroleum jelly should then be applied to the nail bed, using the technique shown in FIG. 2. The operator's hand is shown holding a small brush 15 for the application of a thin coating. A sable brush 16 is then used to apply an acrylic mass to the nail bed as shown in FIG. 3. This material is made available in separate components, which are combined to produce an initially plastic material curable to a solid state. The most effective technique of this blending of the two components is to dis the brush 16 into the liquid, and then into the powder, which are the two forms in which the components are usually supplied. The brush 16 is dabbed into the powder repeatedly to the point that a ball of the plastic material is developed at the end of the brush, as indicated at 17. This ball is developed in size to apaproximately that of a pea, and is then laterally urged with the brush across the surface of the nail bed so that the area is substantially covered. At this point the plastic mass will have a putty-like consistency, and the nail blank is placed on top of it, and properly positioned. A gentle pressure is applied, and held firmly for at lease five to ten seconds. It is preferable that the nail blank and the plastic mass should then be permitted to set for about five minutes under room temperature conditions, so that the plastic material will have cured to a solid condition. During this time, any portions of the plastic material that have been extruded at the sides and periphery of the nail blank can be trimmed with an appropriate instrument.

By this time, the nail will have bonded securely to the plastic mass. The nail can then be gently rocked from side to side, and front to rear, causing it to separate (along with the plastic mass) at the coating of petroleum jelly, which functions as a parting agent. The nail bed form is thus accurately preserved as an addition to the back of the nail blank. The petroleum jelly is then removed from both the plastic mass and the nail bed, using an appropriate solvent. This can be done best with a small cotton ball. A clinical adhesive is then applied to the nail bed (and/or to the plastic mass), and the assembly of the nail blank and the plastic mass is then re-positioned on the nail bed with a gentle pressure sufficient to thoroughly engage the adhesive. Excess extrusions of the adhesive can be removed with an instrument such as an orange wood stick. The installation of the nail is now structurally completed.

It is advisable to then apply a priming coat to the new artificial nail, to seal it against moisture, and prepare it for the application of polish. The sealing material can be of a type commonly used for the cosmetic treatment of fingernails. After the primer (sealer) has properly set, polish can be applied according to preference.

An obvious characteristic of clinical adhesive is that it can be removed without damage to the body tissue. This makes it possible to remove the nail-plastic combination from its position on the nail bed, preferably with the application of a solvent for the clinical adhesive. The solvent can be worked in around the periphery, accompanied by the lateral and front-rear rocking action previously described to work the solvent in toward the central area. The nail can then be removed for cleaning or minor alteration. It can be re-installed by a new application of clinical adhesive in the same manner as before. The nail and the surrounding area, including the nail bed, should be cleaned frequently using this procedure. Whenever the polish is removed from the artificial nail, the primer-sealer should be renewed to inhibit the entrance of moisture. Whenever polish is removed, a non-acetone, or non-damaging, remover is recommended.

It should be noted that the preliminary preparation involving the application of the anti-bactarial solution might conceivably be replaced by the incorporation of some such material in the plastic mass; but at the present state of development, this has not appeared to be practical.

We claim:

1. A method of installing an artificial nail on the nail bed of a finger or toe in the absence of the natural nail, comprising:
    applying a separating agent to said nail bed;
    applying a mass of initially plastic material to said nail bed;
    pressing an artificial nail onto said mass during the plastic condition thereof, and bonding said nail to said mass on solidification of said mass;
    removing said mass and said nail together from said nail bed;
    removing the residue of said separating agent from said nail bed and said mass;
    coating at least one of said nail bed and the inside face of said mass with an adhesive; and
    pressing said nail and said mass in position on said nail bed.

2. A method as defined in claim 1, preceded by treating said nail bed with a disinfectant.

3. A method as defined in claim 1, wherein said artificial nail is roughened on the back thereof prior to being engaged with said mass.

4. A method as defined in claim 1 wherein said separating agent is a petroleum jelly.

5. A method as defined in claim 1, additionally including the application of a sealant to said nail after installation thereof as defined in claim 1 to seal it against moisture.

6. A method as defined in claim 1, additionally including the removal of said nail and mass by application of a solvent to said adhesive, and by gently rocking said nail and mass on said nail bed to work said solvent inward from peripheral areas.

* * * * *